United States Patent [19]

Nageris

[11] Patent Number: 5,219,568
[45] Date of Patent: Jun. 15, 1993

[54] PHARMACEUTICAL COMPOSITION FOR TREATING ACUTE DYSPHONIA

[76] Inventor: Israel Nageris, 14 Brandeis Street, Tel-Aviv, Israel

[21] Appl. No.: 505,454

[22] Filed: Apr. 6, 1990

[51] Int. Cl.$^5$ .................. A61K 37/547; A61K 31/56; A61K 31/525; A61K 31/505
[52] U.S. Cl. ................... 424/94.2; 424/94.64; 514/171; 514/179; 514/251; 514/276; 514/718
[58] Field of Search ............... 424/94.2, 94.64; 514/276, 718, 251, 171, 179

[56] References Cited

PUBLICATIONS

Svirskii, Biol. Abstracts, vol. 72, No. 82144 (1981).
Miyakogawa et al, Biol. Abstracts, vol. 71, No. 40002 (1981).
Ito et al, Biol. Abstracts, vol. 84, No. 39420 (1987).
Bienenstock et al, Biol. Abstracts, vol. 65, No. 44078 (1977).
Damonte et al, Biol. Abstracts, vol. 52, No. 111995 (1970).
Polli, Biol. Abstracts, vol. 81, No. 46395, (1985).

*Primary Examiner*—Jacqueline Stone
*Attorney, Agent, or Firm*—Oblon, Spivak, McClelland, Maier & Neustadt

[57] ABSTRACT

A pharmaceutical composition for the treatment of hoarseness. The composition is administered orally in unit dosage form. It is based on the combination of Varidase (a combination of streptokinase and streptodornase), an antiinflammatory corticosteroid, an antihistamine and an expectorant. The composition may optionally contain vitamins, like vitamin $B_1$ or Vitamin $B_2$. The invention further relates to a method for the treatment of hoarseness in humans, which comprises administering an effective quantity of a composition as defined above.

12 Claims, No Drawings

PHARMACEUTICAL COMPOSITION FOR TREATING ACUTE DYSPHONIA

FIELD OF THE INVENTION

There is provided a pharmaceutical composition, mainly for oral application, for the therapy of hoarseness, either acute or chronic. Such syndrome may be due, amongst others, to edema, hematom or formation of small-size nodules on the vocal cords. The compositions afford a speedy effect, resulting in a rapid alleviation of symptoms and frequently in a cure of the underlying causes of this syndrom.

BACKGROUND OF THE INVENTION

Hoarseness (dysphonia) which is manifest as an unnaturally deep of harsh quality of the voice, and in extreme cases, in practically "loss of voice" is usually the cardinal symptom of laryginal disease, but may also be the manifestation of other disorders. Amongst possible causes there may be mentioned local and constitutional infectious processes, such as acute and chronic laryngitis; neurogenic disorders including hysteria, allergy, etc.

Conventional therapy consists mainly of resting the voice, use of mild sedatives, steam and other inhalations, and other symptomatic measures.

With certain persons, such as actors and politicians, the rapid alleviation of hoarseness may be critical and of paramount importance.

The pharmaceutical compositions of the invention have been developed and tested, and it has been found that they rapidly alleviate hoarseness and restore the normal voice of the patient in a comparatively short period of treatment.

SUMMARY OF THE INVENTION

There are provided pharmaceutical compositions for the treatment of hoarseness. There is provided a method for the treatment of, and alleviation of the symptoms of hoarseness in humans.

The compositions are given orally and result in a large percentage of cases in a rapid alleviation of symptoms, and in a rapid restoration of the voice quantity to normal or nearly normal.

The compositions of the invention are based on a combination of constituents which exert a combined, synergistic action. The main constituents are adapted to dissolve blood clots, to effect an anti-inflammatory action and to provide anti-histaminic activity. Amongst additional desired optional components are various vitamins of the B group and also expectorants.

Experiments have shown that although alleviation of symptoms may be attained with a variety of constituents defined in general terms above, test results are obtained with certain specific drugs, the combination of which provides rapid, and even dramatic results.

Amongst preferred components of the compositions of the invention are:

a. Varidase, which is a mixture of streptokinase and streptodornase, comprising about 5000 to 12000 units streptokinase and about 2000 to 3000 units of streptodornase.

b. Anti-inflammatory corticosteroid of the prednisone type, constituting generally from about 3 to 8 mg prednisone, or an equivalent of another corticosteroid.

c. An antihistamine, such as mebyhdrolin, generally as mebhydrol in napadiysilate; about 30 to 80 mg.

d. Optionally Vitamin $B_2$, from 3 to 10 mg.

e. Vitamin $B_1$, from 10 to 30 mg;

f. An expectorant, such as guaiphenesin, about 40 to 60 mg, of excipient or carrier.

The above compositions are given orally in unit disage forms, which according to a preferred embodiment of the invention, comprise a total of about 250 mg. which contain about 7000 to 10000 streptokinase, 2500 units streptodornase, 5 mg prednisone, 30 to 50 mg of mebhydrolin napadisylate; about 15=20 mg Vitamin $B_1$, about 5 mg Vitamin $B_2$, and about 30 to 70 mg guaiphenesin, in a suitable carrier or excipient.

Varidase results in defibrinogenation of thrombosis or pulmonary emboli and removes artherial occlusions. In the compositions of the invention it exerts an antithrombic and antiinflammatory effect; the prednisone is one of the steroids of choice and exerts a pronounced antiinflammatory effect; the specific antihistamine has been proven to be a preferred drug out of a variety of available antihistamines. It exerts a rapid alleviation of allergic reactions or disturbances causing edema of the nasal mucosa and other tissues; Vitamin $B_2$ (riboflavin) enhances the effect of the other drugs and its lack causes glossitis; Vitamin $B_1$ (thiamine) also provides an enhanced effect, ad its lack causes neuritis. The expectorant is effective in cases of inflammations of the pharynx, in cases of bronchitis and tracheitis.

EXAMPLE

Tablets were prepared containing each:

| Varidase (8000 units streptokinase, 2500 units strentodornase) | |
|---|---|
| Prednisone | 5 mg |
| Mebhydroline | 50 mg |
| Guaiphenesin | 30 mg |
| Excipient up to | 150 mg |

The tablets were administered 3 times a day and resulted in a rapid clearing up of the hoarseness of the patient.

The novel compositions are taken 2 to 3 times daily. The drug can be provided in the form of tablets or as powder in capsules. Administration about one and a half hour before the scheduled appearance of an actor in theatre generally results in the restoration of a normal voice. The drug is of importance for many professions, as set out above, and also for teachers, orators and the like. The above is by way of example and changes in the exact compositions can be resorted to without departing from the invention.

I claim:

1. A pharmaceutical composition for restoring normal voice, in cases of acute dysphonia, which is in tablet or capsule form, which comprises in powder form a combination of each of the following ingredients, effective for said restoration of voice:

a) 5,000 to 12,000 units of streptokinase and 2,000 to 3,000 units of streptodornase;

b) 3 to 8 mg of prednisone; and c) 30 to 80 mg of mebhydrolin napadisylate.

2. The pharmaceutical composition of claim 1, which further contains Vitamins $B_1$ or $B_2$ or both.

3. The pharmaceutical composition of claim 1, which further contains gauiphenesin.

4. The pharmaceutical composition of claim 1, which further contains from 3 to 10 mg of Vitamin $B_2$, from 10 to 30 mg of Vitamin $B_1$ and 40 to 60 mg of guaiphenesin.

5. The pharmaceutical composition of claim 4, which contains per unit dosage about 8,000 units of streptokinase, about 2,500 units of streptodornase, about 5 mg of prednisone, about 30 to 50 mg of mebhydrolin napadisylate, about 5 mg Vitamin $B_2$, about 15 to 20 mg of Vitamin $B_1$ and about 50 mg of guaiphenesin.

6. The pharmaceutical composition according to claim 1, wherein 8,000 to 12,000 units of streptokinase are used.

7. The composition according to claim 1, in capsule form, containing in combination 10,000 units of streptokinase, 2,500 units of streptodornase, 5 mg of prednisone and 50 mg of mebhydrolin napadisylate.

8. A method for restoring normal voice, in cases of acute dysphonia, which comprises administering to a human in tablet or need thereof an effective amount of a pharmaceutical composition, which is in capsule form, comprising a powder to form a combination of each of the following ingredients, effective for said restoration of voice:
 a) 5,000 to 12,000 units of streptokinase and 2,000 to 3,000 units of streptodornase;
 b) 3 to 8 mg of prednisone; and
 c) 30 to 80 mg of mebhydrolin napadisylate.

9. The method according to claim 8, wherein said composition used contains 8,000 to 12,000 units of streptokinase.

10. The method of claim 8, wherein said composition further contains Vitamin $B_1$ or $B_2$ or both.

11. The method of claim 8, wherein said composition further contains guaiphenesin.

12. The method of claim 8, wherein said composition is administered three times per day to said human.

* * * * *